US012576241B2

(12) United States Patent
Chiu et al.

(10) Patent No.: US 12,576,241 B2
(45) Date of Patent: Mar. 17, 2026

(54) DETACHABLE URETHRAL CATHETERIZATION DEVICE

(71) Applicant: GUDENG PRECISION INDUSTRIAL CO., LTD, New Taipei (TW)

(72) Inventors: Ming-Chien Chiu, New Taipei (TW); Yung-Chin Pan, New Taipei (TW); Chia-Ch Lin, New Taipei (TW); Chi-Lin Li, New Taipei (TW); Meng-Hsuan Lu, New Taipei (TW)

(73) Assignee: GUDENG PRECISION INDUSTRIAL CO., LTD, New Taipei (TW)

( * ) Notice: Subject to any disclaimer, the term of this patent is extended or adjusted under 35 U.S.C. 154(b) by 361 days.

(21) Appl. No.: 18/526,304

(22) Filed: Dec. 1, 2023

(65) Prior Publication Data

US 2025/0161633 A1 May 22, 2025

(30) Foreign Application Priority Data

Nov. 16, 2023 (TW) ................................. 112144393

(51) Int. Cl.
*A61M 25/01* (2006.01)
*A61M 25/00* (2006.01)

(52) U.S. Cl.
CPC .... *A61M 25/0116* (2013.01); *A61M 25/0017* (2013.01); *A61M 2205/10* (2013.01);
(Continued)

(58) Field of Classification Search
CPC .......... A61M 25/0116; A61M 25/0017; A61M 25/0113; A61M 2202/0496;
(Continued)

(56) References Cited

U.S. PATENT DOCUMENTS

2006/0041245 A1* 2/2006 Ferry ................. A61B 17/3403
604/95.01
2013/0274657 A1* 10/2013 Zirps ................ A61M 25/0147
604/95.01
(Continued)

FOREIGN PATENT DOCUMENTS

CN 213432048 U 6/2021
CN 113633389 A * 11/2021 ...... A61M 25/09041
(Continued)

*Primary Examiner* — Adam Marcetich
(74) *Attorney, Agent, or Firm* — ScienBiziP, P.C.

(57) ABSTRACT

A detachable urethral catheterization device for guiding a movement of a urinary catheter is provided. The detachable urethral catheterization device includes a conveying body and a clamping module. The conveying body includes a driving module, a conveying channel, and a module accommodating groove in communication with the conveying channel, the module accommodating groove including a first coupling component. The clamping module coupled to the driving module, and having a second coupling component, where the second coupling component is detachably coupled to the first coupling component in the module accommodating groove, and where the driving module is configured to control the clamping module to clamp the urinary catheter and move the urinary catheter in the conveying channel and the module accommodating groove.

10 Claims, 12 Drawing Sheets

10

(52) U.S. Cl.
  CPC ... *A61M 2205/33* (2013.01); *A61M 2205/502*
  (2013.01); *A61M 2210/1078* (2013.01)

(58) Field of Classification Search
  CPC ...... A61M 2210/1096; A61M 25/0111; A61M
  2025/0681; A61M 2205/10; A61M
  2210/1092; A61M 25/01; A61M
  2210/1078; A61M 2210/1085; A61M
  2210/1089
  See application file for complete search history.

(56) References Cited

U.S. PATENT DOCUMENTS

| | | | | |
|---|---|---|---|---|
| 2019/0192822 A1* | 6/2019 | Kim | ....................... | A61L 29/041 |
| 2021/0045824 A1* | 2/2021 | Landey | ................... | A61G 13/04 |
| 2022/0387756 A1 | 12/2022 | Wang et al. | | |
| 2024/0206998 A1* | 6/2024 | Deng | ..................... | A61B 34/76 |
| 2024/0226501 A1* | 7/2024 | Amar | ..................... | A61M 1/87 |
| 2025/0152921 A1* | 5/2025 | Liu | ........................ | A61B 34/00 |

FOREIGN PATENT DOCUMENTS

| | | | | | | |
|---|---|---|---|---|---|---|
| CN | 114224492 A | * | 3/2022 | ............. | A61B 34/70 |
| CN | 115591083 A | * | 1/2023 | ........ | A61M 25/0113 |
| CN | 116196110 A | * | 6/2023 | ............. | A61B 34/30 |
| CN | 116392702 A | * | 7/2023 | ........ | A61M 25/0113 |
| CN | 116637271 A | * | 8/2023 | ........ | A61M 25/0113 |
| WO | 0197896 A1 | | 12/2001 | | |

\* cited by examiner

10

DETACHABLE URETHRAL CATHETERIZATION DEVICE

CROSS-REFERENCE TO RELATED APPLICATION(S)

This application claims the benefit of and priority to Taiwan Patent Application Serial No. 112144393, filed on Nov. 16, 2023, entitled "DETACHABLE CATHETERIZATION DEVICE," the contents of which are hereby incorporated herein fully by reference for all purposes.

FIELD

The present disclosure generally relates to a field of detachable urethral catheterization devices and, more particularly, to a clamping module that facilitates quick replacement and/or cleaning of a urinary catheter, and a urethral catheterization device including the urinary catheter, which is operable by a user.

BACKGROUND

When a user experiences difficulty in urination, in order to facilitate the smooth discharge of urine from the patient's bladder, it is necessary for healthcare providers to perform urethral catheterization on the patient. Healthcare providers may insert a urethral catheter, through the patient's urethra, into the bladder to assist in the external drainage of urine. Since the urinary catheter is soft, the insertion process into the urethral opening of a male patient may be prone to inaccuracies due to the proficiency of manual handling. This may necessitate repeated attempts, leading to discomfort for the patient.

To address the shortcomings of manual procedures, urinary catheterization devices have been developed as assistive tools for urinary catheter insertion. However, users may only undergo urinary catheterization device operations with assistance received from healthcare providers, for example, in a hospital setting. Additionally, existing urinary catheterization devices have integrated transport mechanisms for holding the urinary catheter, and these mechanisms may not be detached, for example, for cleaning. The transport mechanisms, particularly those used for clamping the catheter, are prone to accumulating dirt, and are challenging to be cleaned thoroughly. Specific cleaning tools are required to clean these transport mechanisms. However, even with the use of specific cleaning tools, effectively cleaning (e.g., the dirt) in the crevices of the device is challenging, rendering the crevices prone to bacterial growth. This may result in the contamination of the urinary catheter, increasing the risk of bacterial infection for the user. Therefore, addressing the difficulty in cleaning urinary catheterization devices and enhancing operational convenience is a pressing issue.

SUMMARY

In view of the above, there is a need in the field to provide a detachable urinary catheterization device that is easy for users to operate independently and is also easy to clean/ sterilize.

In a first aspect of the present disclosure, a detachable urethral catheterization device for guiding a movement of a urinary catheter is provided. The urethral catheterization device includes: a conveying body including a driving module, a conveying channel, and a module accommodating groove in communication with the conveying channel, the module accommodating groove including a first coupling component; and a clamping module coupled to the driving module, the clamping module having a second coupling component, where the second coupling component is detachably coupled to the first coupling component in the module accommodating groove, and the driving module is configured to control the clamping module to clamp the urinary catheter and move the urinary catheter in the conveying channel and the module accommodating groove.

In another implementation of the first aspect, the first coupling component and the second coupling component are matching magnetic components, and the clamping module is defined as detachable via a magnetic attraction between the first coupling component and the second coupling component.

In another implementation of the first aspect, the clamping module includes a clamping body positioned within the module accommodating groove, the clamping body having a clamping channel that is correspondingly positioned within the conveying channel, and that is configured to accommodate the urinary catheter; a main driving component configured to couple to the driving module; and an auxiliary driving component, where the main driving component and the auxiliary driving component are respectively located at two sides of the clamping channel, the main driving component and the auxiliary driving component contact an outer side of the urinary catheter, the driving module is configured to control the main driving component to move the urinary catheter, and the auxiliary driving component synchronously provides a moving assistance force based on a movement state of the urinary catheter.

In another implementation of the first aspect, the clamping channel is equipped with a limiting portion, and the limiting portion is configured to limit a moving direction and a deviation of the urinary catheter.

In another implementation of the first aspect, the main driving component comprises a first coupling portion, the driving module comprises a second coupling portion, the first coupling portion and the second coupling portion include matching coupling structures, and when the first coupling portion is correspondingly coupled to the second coupling portion, the main driving component is coupled and fixed to the driving module.

In another implementation of the first aspect, the first coupling portion has a guiding inclined surface, and the guiding inclined surface is configured to guide the second coupling portion to be coupled and fixed to a coupling position of the first coupling portion.

In another implementation of the first aspect, the clamping module is positioned within the module accommodating groove, a gap is between two outer sides of the clamping module and an inner wall of the module accommodating groove, and the gap is configured to ensure a central axis of the conveying channel and a central axis of the urinary catheter are coaxial.

In another implementation of the first aspect, the conveying channel includes a urinary catheter guiding portion and a urinary sheath accommodating portion, the module accommodating groove is located between the urinary catheter guiding portion and the urinary sheath accommodating portion, the urinary catheter guiding portion is configured to guide a movement path of the urinary catheter, the urinary sheath accommodating portion is configured to accommodate a urinary sheath, and a central axis of a through-hole of the urinary sheath is coaxial with a central axis of the urinary catheter.

In another implementation of the first aspect, the clamping module includes a manual adjustment component, the manual adjustment component is configured to manually adjust a clamping force between the clamping module and the urinary catheter, and a movement range of the urinary catheter between the conveying channel and the module accommodating groove.

In another implementation of the first aspect, the conveying body further includes: a main controller electrically connected to the driving module, the main controller configured to control an operation of the driving module; a speed controller electrically connected to the main controller, the main controller controlling a driving operation of the driving module according to an operating speed and mode of the speed controller; a power controller configured to provide a power for an operation of components of the conveying body; and a display electrically connected to the main controller, the display configured to display an operational state of the conveying body.

BRIEF DESCRIPTION OF THE DRAWINGS

The present disclosure will be better understood from the following detailed description read in light of the accompanying drawings, where.

DETAILED DESCRIPTION

Figure 1:
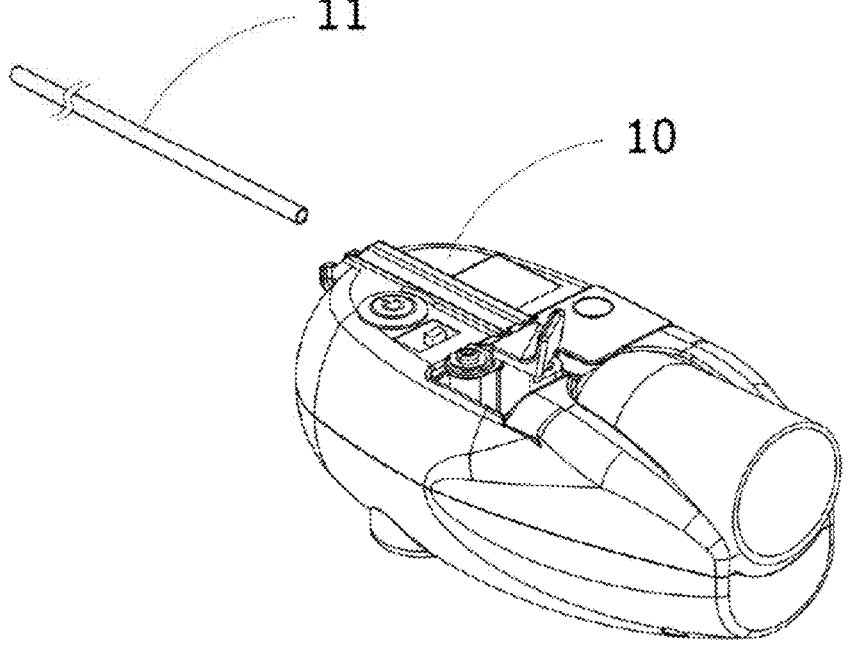
FIG. 1 illustrates a schematic view of a detachable urinary catheterization device, according to an example implementation of the present disclosure.

The following disclosure contains specific information pertaining to exemplary implementations in the present disclosure. The drawings in the present disclosure and their accompanying detailed disclosure are directed to merely exemplary implementations. However, the present disclosure is not limited to merely these exemplary implementations. Other variations and implementations of the present disclosure will occur to those skilled in the art. Unless noted otherwise, like or corresponding components among the figures may be indicated by like or corresponding reference numerals. Moreover, the drawings and illustrations in the present disclosure are generally not to scale and are not intended to correspond to actual relative dimensions.

For the purposes of consistency and ease of understanding, like features are identified (although, in some examples, not shown) by numerals in the exemplary figures. However, the features in different implementations may be different in other respects, and thus shall not be narrowly confined to what is shown in the figures.

The disclosure uses the phrases "in one implementation," "in some implementations," and so on, which may each refer to one or more of the same or different implementations. The term "coupled" is defined as connected, directly, or indirectly through intervening components, and is not necessarily limited to physical connections. The term "comprising" means "including, but not necessarily limited to;" it specifically indicates open-ended inclusion or membership in the so-described combination, group, series, and the equivalent.

Additionally, for the purposes of explanation and non-limitation, specific details, such as functional entities, techniques, protocols, standards, and the like, are set forth for providing an understanding of the described technology. In other examples, detailed disclosure of well-known methods, technologies, systems, architectures, and the like are omitted so as not to obscure the disclosure with unnecessary details.

FIG. 1 illustrates a schematic view of a detachable urinary catheterization device, according to an example implementation of the present disclosure. Specifically, FIG. 1 illustrates the detachable urinary catheterization device 10 of the present disclosure along with the urinary catheter 11. The detachable urinary catheterization device 10 is configured to guide the movement of the urinary catheter 11. Users may hold the detachable urinary catheterization device 10 and insert one end of the urinary catheter 11 into the detachable urinary catheterization device 10. Then the other end of the urinary catheter 11 is inserted into the urethral opening of the user's genitalia for urination (e.g., after an operation is performed on the user).

Figure 2:
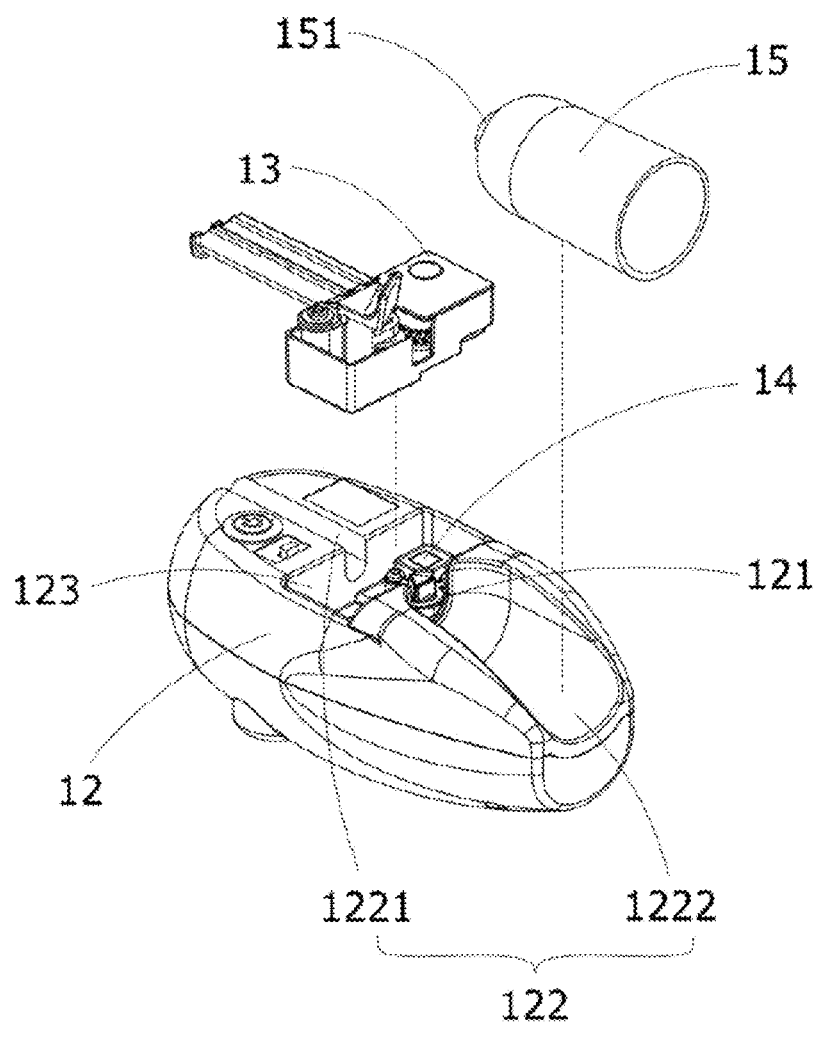
FIG. 2 illustrates an exploded schematic view of the detachable urinary catheterization device, according to an example implementation of the present disclosure.
Figure 3:
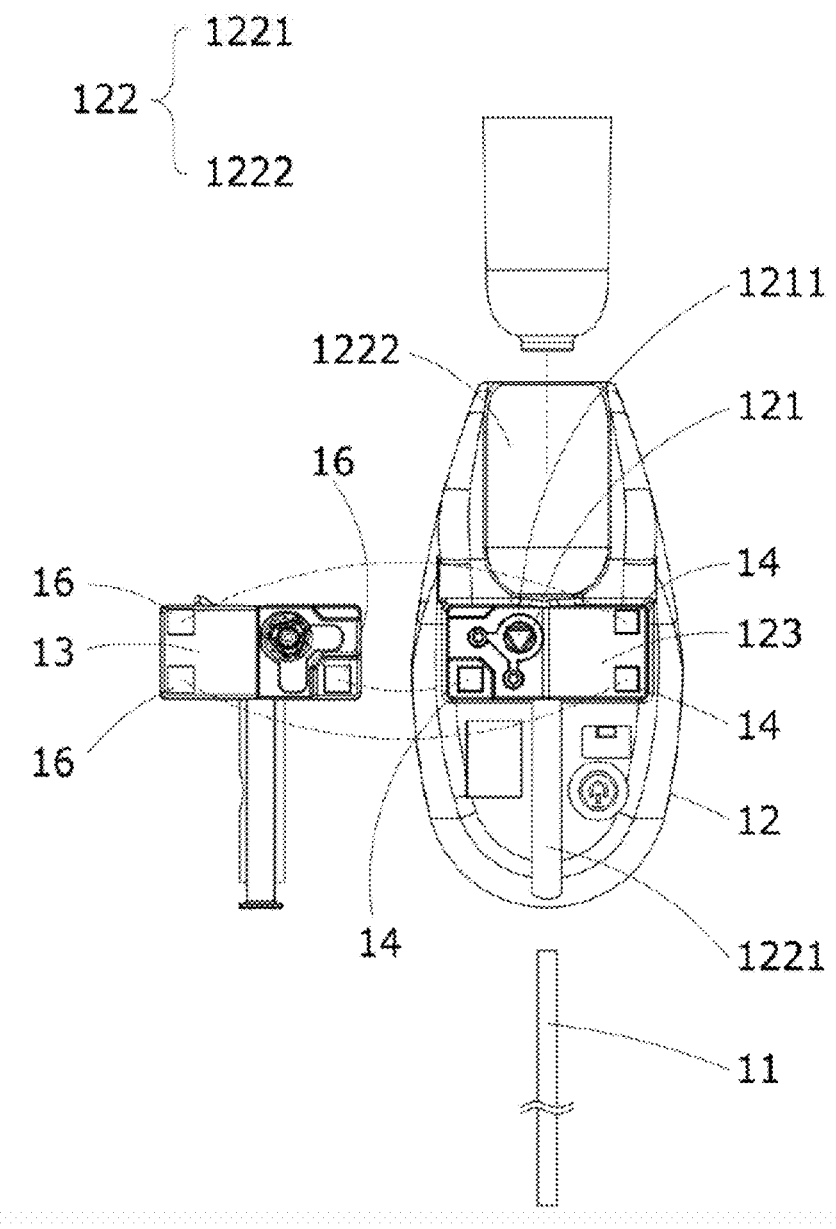
FIG. 3 illustrates a schematic distribution of a first coupling component and a second coupling component, according to an example implementation of the present disclosure.

FIG. 2 illustrates an exploded schematic view of the detachable urinary catheterization device, according to an example implementation of the present disclosure. FIG. 3 illustrates a schematic distribution of a first coupling component and a second coupling component, according to an example implementation of the present disclosure. With reference to FIGS. 2 and 3, the detachable urinary catheterization device 10 includes a conveying body 12 and a clamping module 13. The conveying body 12 includes a driving module 121, a conveying channel 122, and a module accommodating groove 123. The conveying channel 122 is connected to the module accommodating groove 123, and the module accommodating groove 123 is provided with a first coupling component 14. The number of the first coupling component 14 may be one or more, depending on the requirements, and is not limited to a specific number. The conveying channel 122 includes a urinary catheter guiding portion 1221 and a urinary sheath accommodating portion 1222. The module accommodating groove 123 is located between the urinary catheter guiding portion 1221 and the urinary sheath accommodating portion 1222. The urinary catheter guiding portion 1221 is configured to guide the movement path of the urinary catheter 11, and the urinary sheath accommodating portion 1222 is configured to accommodate a urinary sheath 15. The central axis of the through-hole 151 of the urinary sheath 15 is coaxial with the central axis of the urinary catheter 11.

The clamping module 13 is coupled to the driving module 121, and the clamping module 13 operates under the driving force of the driving module 121. The driving module 121 may be used to control the clamping module 13 to clamp the urinary catheter 11 and move the urinary catheter 11 in the conveying channel 122 and the module accommodating groove 123. The clamping module 13 is provided with a second coupling component 16. The number and position of the second coupling component 16 corresponds to the first coupling component 14. The clamping module 13 utilizes the second coupling component 16 to combine and remove the first coupling component 14 of the module accommodating groove 123, where the second coupling component 16 corresponds to the first coupling component 14, which allows the clamping module 13 to be individually detached for subsequent cleaning. In some implementations, the first coupling component 14 and the second coupling component 16 are matching magnetic components, defining the clamping module 13 as detachable through magnetic attraction. Specifically, both the first coupling component 14 and the second coupling component 16 may be magnetic elements capable of mutual magnetic attraction. Alternatively, one of the first coupling component 14 and the second coupling component 16 may be a magnetic element, and the other may be a metal component that may be magnetically attracted by the magnetic element. The coupling structure and types of the first coupling component 14 and the second coupling component 16 are not limited to magnetic elements. In addition, other quick-detach and assembly structures, such as quick-release buckle structures, may be used in the first coupling component 14 and the second coupling component 16.

Figure 4:
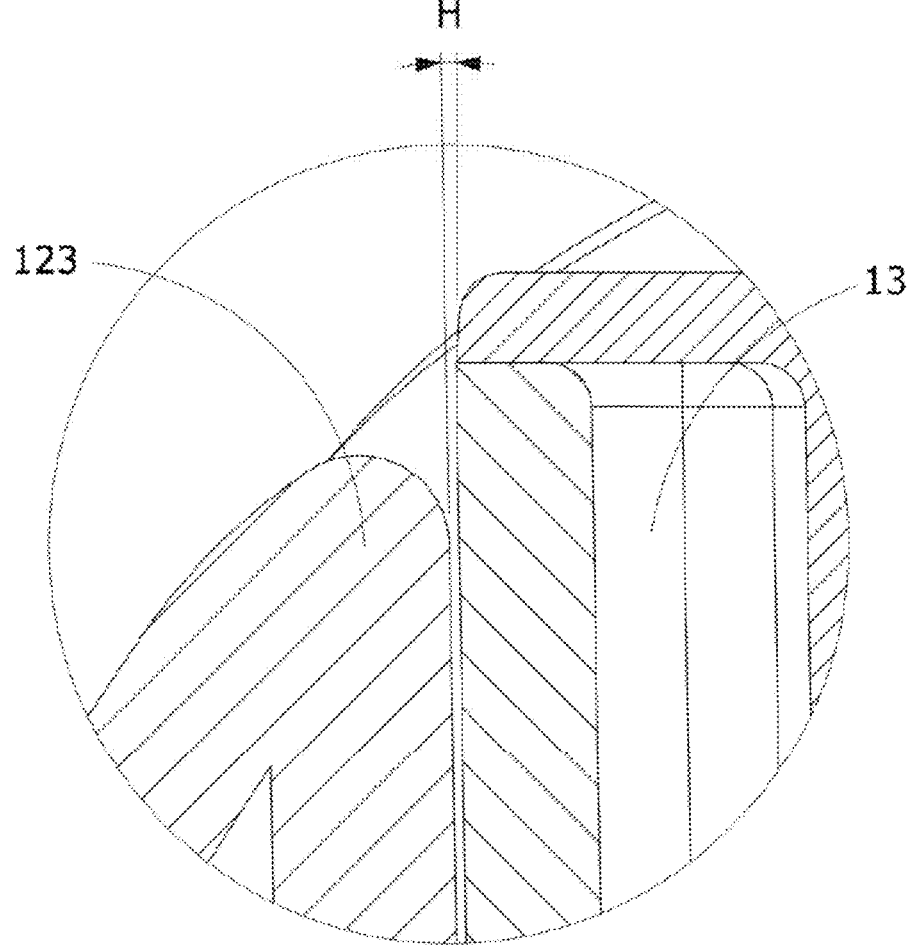
FIG. 4 illustrates a schematic view of the gap between the clamping module and the module accommodating a groove, according to an example implementation of the present disclosure.

FIG. 4 illustrates a schematic view of the gap between the clamping module and the module accommodating a groove, according to an example implementation of the present disclosure. With reference to FIG. 4, in order to prevent the clamping module 13 from deviating after coupling with the module accommodating groove 123, the position of the first coupling component 14, after being coupled to the second coupling component 16, should be arranged to create a gap H, as shown in the figure, between the two sides of the clamping module 13 and the inner wall of the module accommodating groove 123. For example, if the first coupling component 14 and the second coupling component 16 have a magnetic structure, the design of the gap H may be used to control the displacement in the X and Y axes of the clamping module 13. In the Z-axis direction, the clamping module 13 will not fall off from the module accommodating groove 123 due to the magnetic attraction. When the clamping module 13 is coupled to the module accommodating groove 123, the gap H is configured to ensure the central axis of the conveying channel 122 and the central axis of the urinary catheter 11 are coaxial. In other words, the present disclosure primarily utilizes the gap formed between the module accommodating groove 123 and the clamping module 13 to prevent deviation of the clamping module 13 and to ensure an accurate alignment of the urinary catheter 11. The optimal distance for the gap H is preferably less than or equal to 0.1 mm. The present disclosure is not limited to the first coupling component 14 and the second coupling component 16 being of a magnetic structure. As long as a gap H may be provided between the two sides of the clamping module 13 and the inner wall of the module accommodating groove 123, such a design falls within the scope of the present disclosure.

Figure 5:
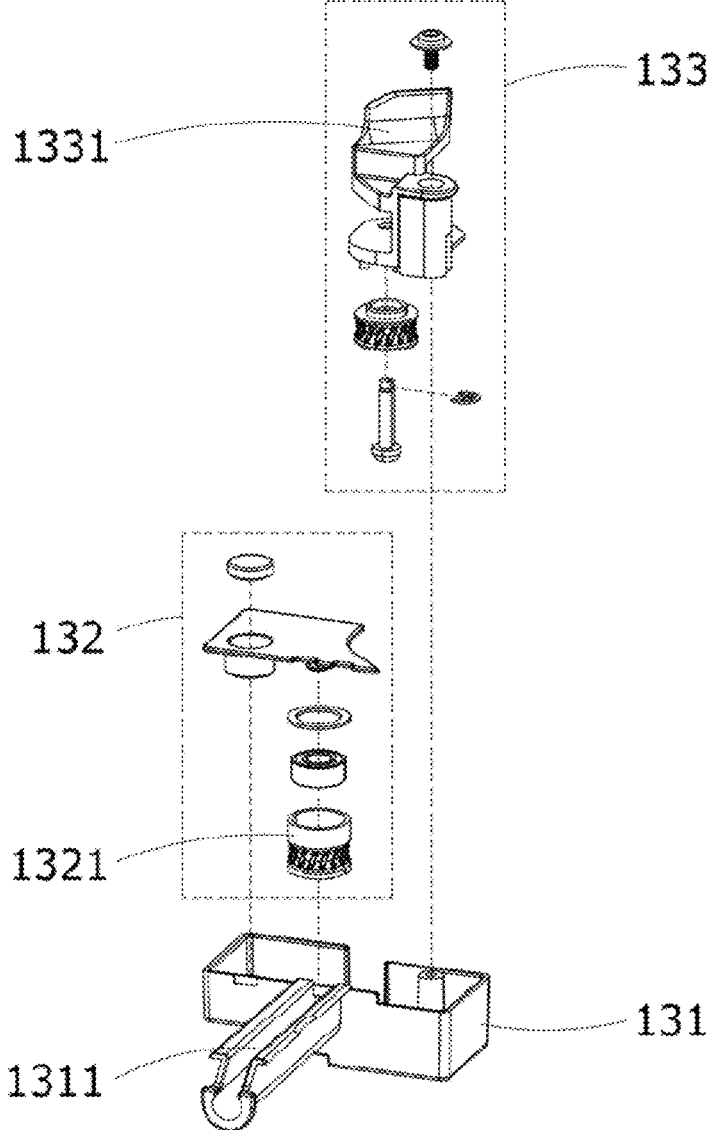
FIG. 5 illustrates an exploded schematic diagram of the structure of the clamping module, according to an example implementation of the present disclosure.

FIG. 5 illustrates an exploded schematic diagram of the structure of the clamping module, according to an example implementation of the present disclosure. With reference to FIGS. 2, 3 and 5, the detailed structure of the clamping module 13 in the present disclosure is described. The clamping module 13 includes a clamping body 131, a main driving component 132, and an auxiliary driving component 133. The clamping body 131 is configured to be placed in the module accommodating groove 123, and the clamping body 131 has a clamping channel 1311. The clamping channel 1311 corresponds to the conveying channel 122 and the clamping channel 1311 extends outward from one side of the clamping body 131. The shape of the clamping channel 1311 is configured to match the urinary catheter guiding portion 1221 of the conveying channel 122. In other words, the clamping channel 1311 may be stacked on the urinary catheter guiding portion 1221 to define the movement path of the urinary catheter 11. The central axis of the through-hole 151 of the urinary sheath 15 is coaxial with the central axis of the urinary catheter 11. This way, the position defined by the urinary catheter guiding portion 1221 and the clamping channel 1311, at one end of the conveying channel 122, is intended for the insertion of the urinary catheter 11. The other end of the conveying channel 122, the urinary sheath accommodating portion 1222, is used to accommodate the urinary sheath 15. The size of the urinary sheath 15 may be changed to a corresponding size based on the dimensions of the user's genitalia. The urinary sheath 15 is positioned to accommodate the user's genitalia.

After inserting the urinary catheter 11 from one end of the urinary catheter guiding portion 1221, urinary catheter 11 advances through the module accommodating groove 123 towards the through-hole 151 of the urinary sheath 15 on the urinary sheath accommodating section portion 1222, the urinary catheter 11 passing through the user's genital urethral opening until urinary catheter 11 reaches the bladder.

Figure 9:
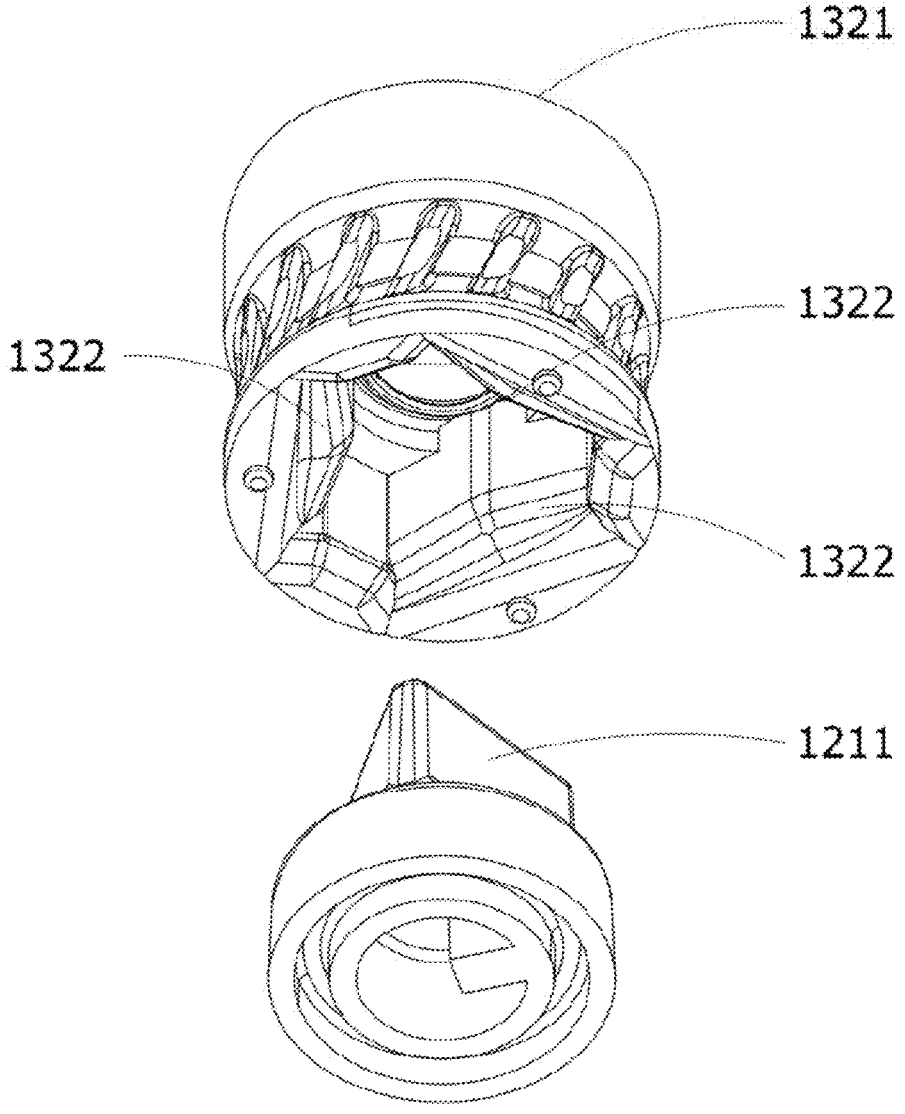
FIG. 9 illustrates a schematic diagram of the combination of the first coupling part and the second coupling part, according to an example implementation of the present disclosure.

FIG. 9 illustrates a schematic diagram of the combination of the first coupling part and the second coupling part, according to an example implementation of the present disclosure. With reference to FIGS. 3, 5, and 9, the main driving component 132 and the auxiliary driving component 133 are both installed in the clamping body 131. The main driving component 132 is configured to couple with the driving module 121. Specifically, the main driving component 132 includes a first coupling portion 1321, and the driving module 121 includes a second coupling portion 1211. The first coupling portion 1321 and the second coupling portion 1211 have matching coupling structures. When the first coupling portion 1321 is coupled with/to the second coupling portion 1211, the main driving component 132 is coupled and fixed to the driving module 121. The first coupling portion 1321 has a guiding inclined surface 1322, which guides the second coupling portion 1211 to be coupled and fixed to the first coupling portion 1321. The first coupling portion 1321 has a free rotation function. When the second coupling portion 1211 rotates along a rotational direction and contacts the guiding inclined surface 1322, the inclined direction of the guiding inclined surface 1322 automatically corrects the orientation relationship between the first coupling portion 1321 and the second coupling portion 1211, completing the coupling of the clamping module 13 and the module accommodating groove 123. Therefore, when the second coupling portion 1211 stops at any angle and couples to the first coupling portion 1321, and when the second coupling portion 1211 contacts the guiding inclined surface 1322 of the first coupling portion 1321, both the second coupling portion 1211 and the first coupling portion 1321 may instantly rotate 360 degrees to correct their orientation, allowing the second coupling portion 1211 to smoothly fit into the first coupling portion 1321.

In some implementations, the main driving component 132 and the auxiliary driving component 133 may be guide wheels, gears, or a combination thereof. The main driving component 132 and the auxiliary driving component 133 are respectively located on two sides of the clamping channel 1311. When the urinary catheter 11 passes through the clamping channel 1311, the main driving component 132 and the auxiliary driving component 133 may simultaneously contact the outer side of the urinary catheter 11. The driving module 121 is used to control the main driving component 132 to move of the urinary catheter 11, and the auxiliary driving component 133 synchronously provides a moving assistance force based on the movement state of the urinary catheter 11.

After the driving module 121 drives the main driving component 132 to operate, the main driving component 132 may press against one side of the urinary catheter 11 and drive the urinary catheter 11 (e.g., to move in a certain direction). At this time, the auxiliary driving component 133 on the opposite side of the main driving component 132 also presses against the other side of the urinary catheter 11 to provide the moving assistance force for the urinary catheter 11. This causes the main driving component 132 to rotate under the drive of the driving module 121, simultaneously driving the urinary catheter 11 to move back and forth along the movement path.

Figure 6:
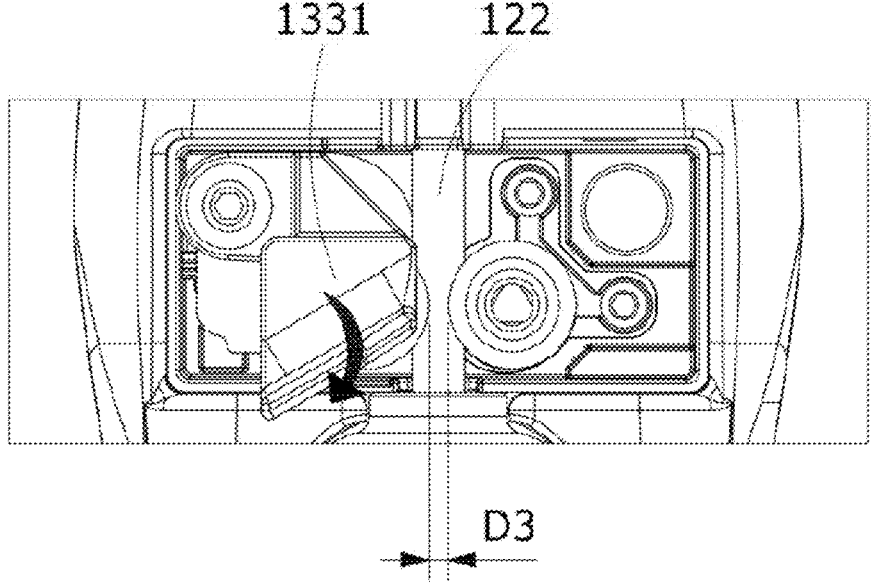
FIG. 6 illustrates the operational process of the manual adjustment component, according to an example implementation of the present disclosure.
Figure 7:
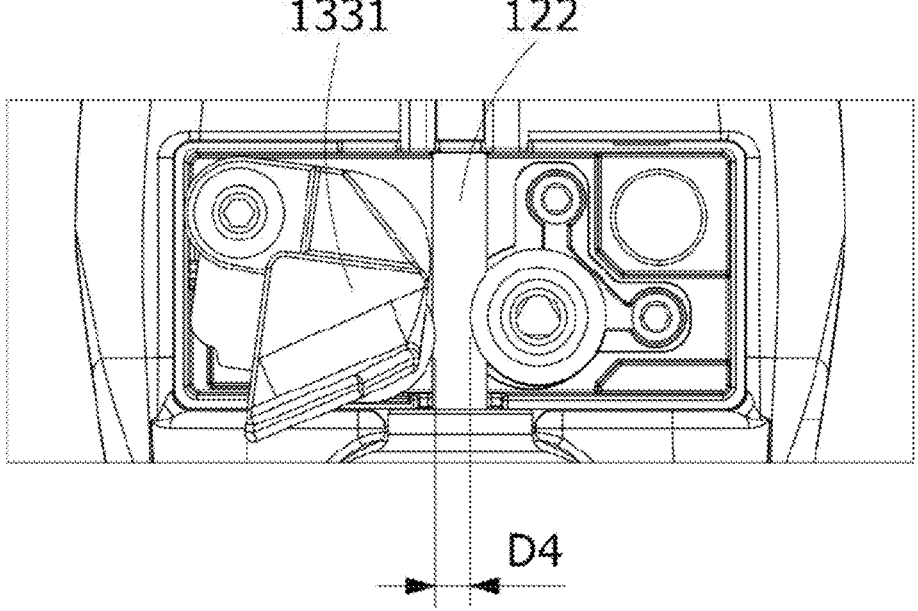
FIG. 7 illustrates the operational process of the manual adjustment component, according to an example implementation of the present disclosure.

FIG. 6 illustrates the operational process of the manual adjustment component, according to an example implementation of the present disclosure. FIG. 7 illustrates the operational process of the manual adjustment component, according to an example implementation of the present disclosure. With reference to FIGS. 3, 5, 6, and 7, the auxiliary driving component 133 of the clamping module 13 also includes a manual adjustment component 1331. The manual adjustment component 1331 is used to manually adjust the clamping force between the clamping module 13 and the urinary catheter 11, and the movement range of the urinary catheter 11 in the conveying channel 122 and the module accommodation groove 123. Since the clamping channel 1311 may be stacked on the urinary catheter guiding portion 1221 to define the movement path of the urinary catheter 11, the urinary catheter 11 may actually move back and forth along the movement path. The manual adjustment component 1331 is coupled to the auxiliary driving component 133, so the auxiliary driving component 133 may be correspondingly driven based on the adjustment range of the manual adjustment component 1331, providing the moving assistance force for the urinary catheter 11.

Specifically, when an abnormality occurs in the movement of the urinary catheter 11, fine adjustments may be made using the manual adjustment component 1331. For example, when the main driving component 132 and the auxiliary driving component 133 clamp the urinary catheter 11, a spacing D3 may be created between the main driving component 132 and the auxiliary driving component 133. Under normal use of the urinary catheter 11, the urinary catheter 11 is usually clamped in the spacing D3. The catheter of the urinary catheter 11 may slightly expand or the diameter of the urinary catheter may vary under different circumstances (e.g., due to the effects of thermal expansion and contraction from urine), causing the urinary catheter 11 to be tightly clamped in the spacing D3 between the main driving component 132 and the auxiliary driving component 133, making it difficult for the urinary catheter 11 to move. Under such a circumstance, the user may adjust the manual adjustment component 1331, causing the auxiliary driving component 133 to shift, thereby adjusting and increasing the range of spacing D3 to spacing D4, where spacing D4 is greater than spacing D3. This allows the urinary catheter 11 to move smoothly without being tightly clamped by the main driving component 132 and the auxiliary driving component 133.

Figure 8:
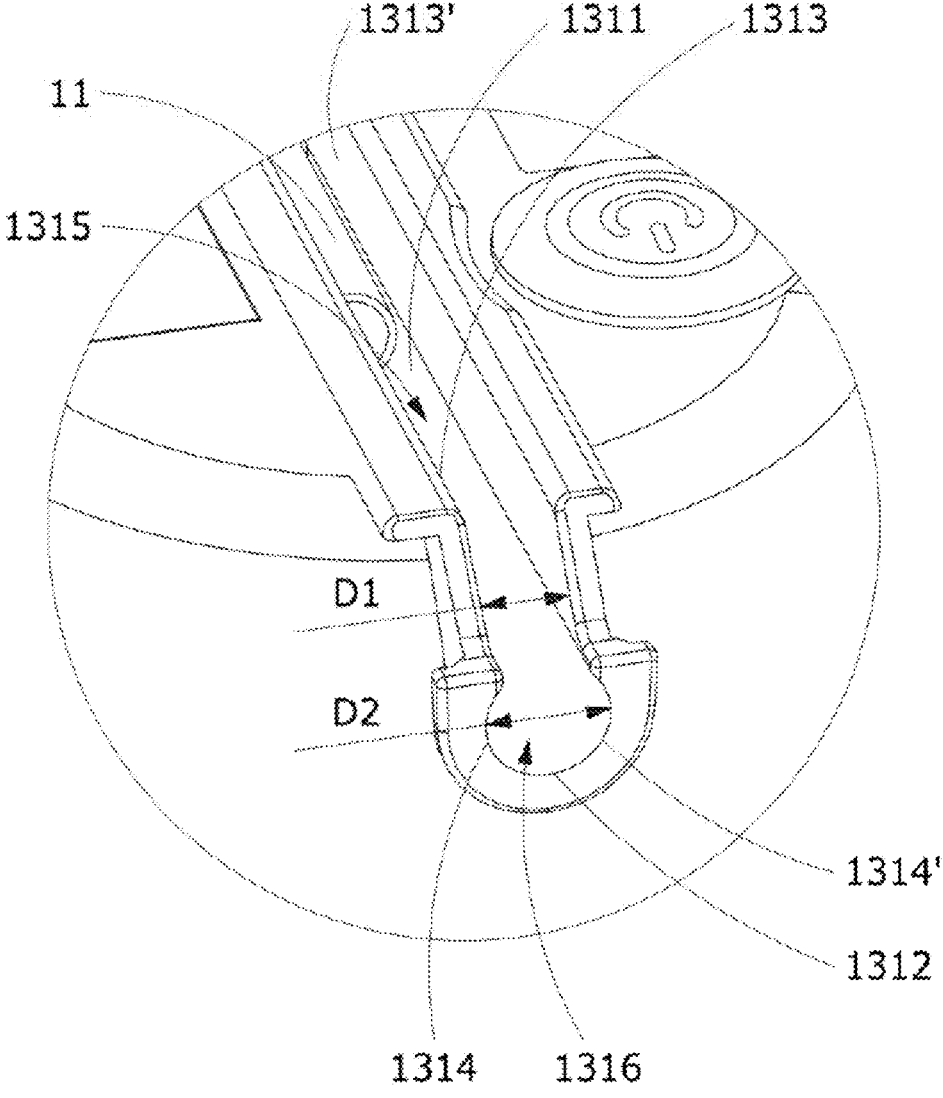
FIG. 8 illustrates a schematic structural diagram of the clamping channel, according to an example implementation of the present disclosure.

FIG. 8 illustrates a schematic structural diagram of the clamping channel, according to an example implementation of the present disclosure. With reference to FIGS. 3, 5, and 8, the clamping channel 1311 may be a semi-open channel. The clamping channel 1311 may be equipped with a limiting portion 1312 to restrict the movement and deviation of the urinary catheter 11. The limiting portion 1312 may be located on the inner side below the clamping channel 1311. Additionally, the limiting portion 1312 and the clamping channel 1311 may be connected. Specifically, there is a spacing D1 between the opposite inner wall surfaces 1313, 1313' of the clamping channel 1311, and a spacing D2 between the opposite inner wall surfaces 1314, 1314' of the limiting portion 1312. Spacing D1 is smaller than spacing D2, and the outer diameter of the urinary catheter 11 is slightly smaller than spacing D2, while the outer diameter of the urinary catheter 11 is greater than spacing D1. Since the outer diameter of the urinary catheter 11 is greater than spacing D1, the urinary catheter 11 may not be directly inserted from the open end 1315 of the clamping channel 1311. The urinary catheter 11 must be inserted from the insertion end 1316 of the limiting portion 1312, aligning the insertion direction of the urinary catheter 11 with the axis of the clamping channel 1311.

Figure 10:
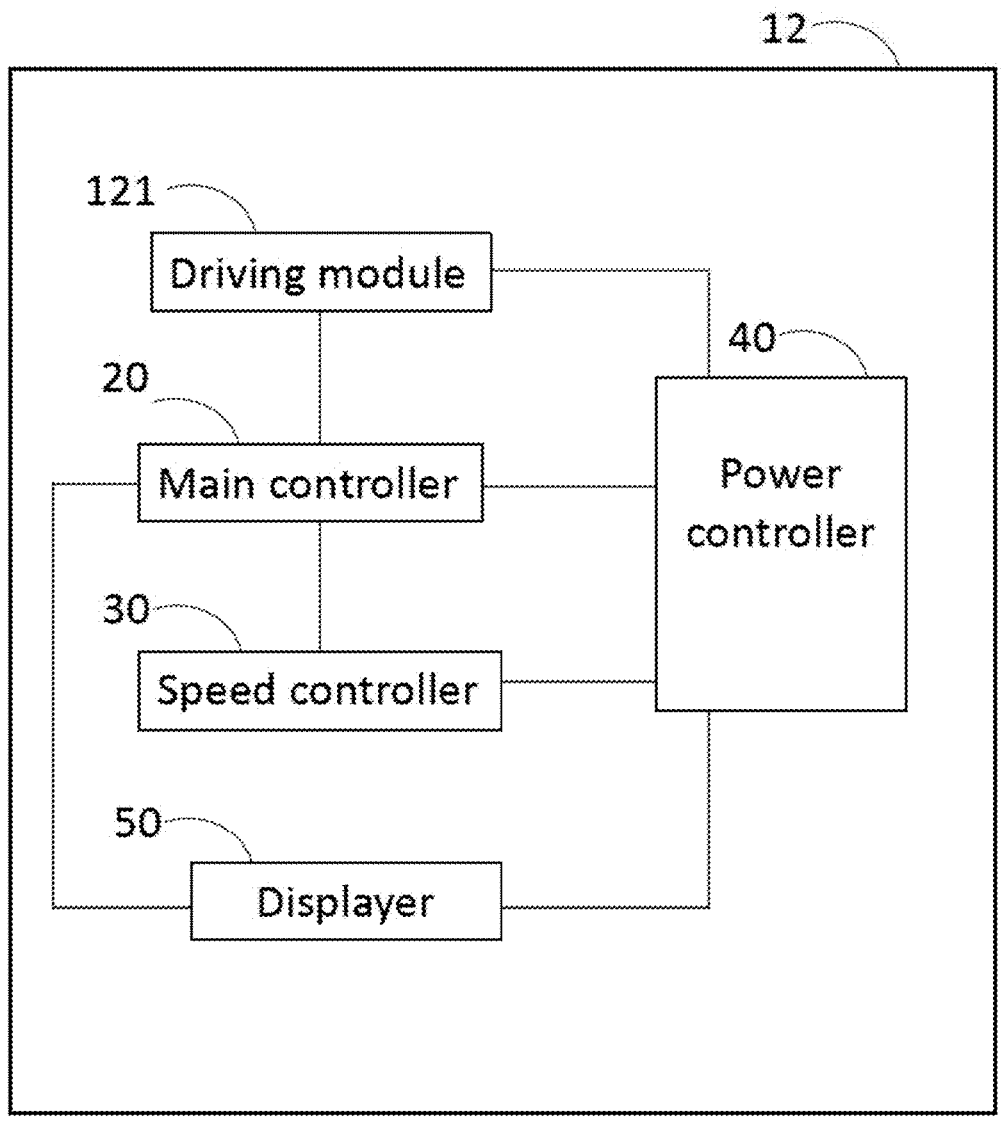
FIG. 10 illustrates a schematic diagram of the electronic module in the conveying body, according to an example implementation of the present disclosure.
Figure 11:
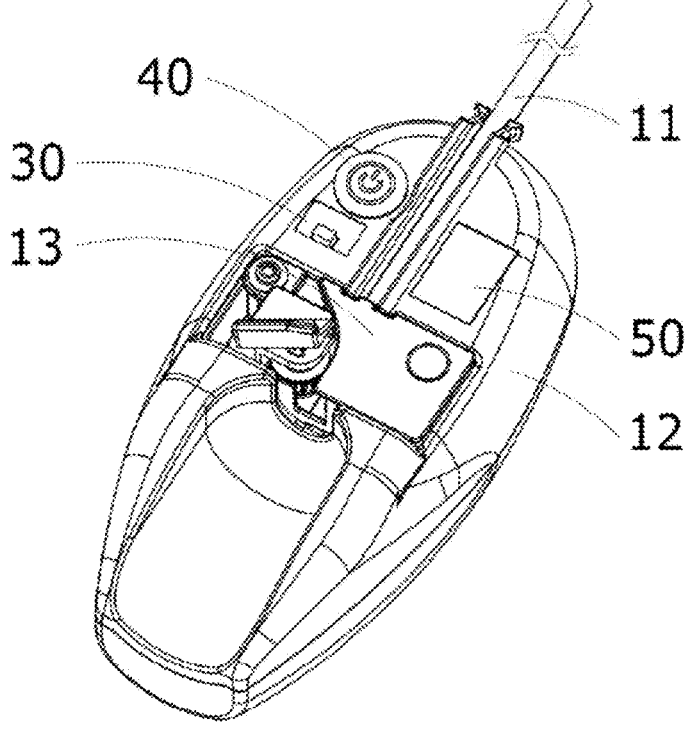
FIG. 11 illustrates a schematic view of the appearance of the conveying body, according to an example implementation of the present disclosure.
Figure 12:
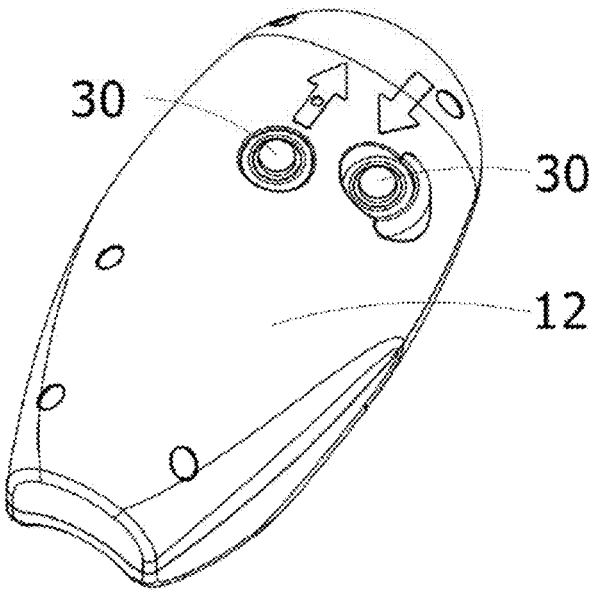
FIG. 12 illustrates a schematic view of the appearance of the conveying body, according to an example implementation of the present disclosure.

FIG. 10 illustrates a schematic diagram of the electronic module in the conveying body, according to an example implementation of the present disclosure. FIG. 11 illustrates a schematic view of the appearance of the conveying body, according to an example implementation of the present disclosure. FIG. 12 illustrates a schematic view of the appearance of the conveying body, according to an example implementation of the present disclosure. With reference to FIGS. 1, 10, 11, and 12, the conveying body 12 further includes a main controller 20, a speed controller 30, a power controller 40, and a display 50. The main controller 20 is electrically connected to the driving module 121 to control the driving operation of the driving module 121. The speed controller 30 is electrically connected to the main controller 20, and the main controller 20 controls the driving operation of the driving module 121, according to the operating speed and mode of the speed controller 30. The modes may include forward, backward, fast, slow, and so on. The power controller 40 provides power for the operation of all components on the conveying body 12. Additionally, the power controller 40 may be connected to the power switch to enable the user to turn the conveying body 12 on or off. The display 50 is electrically connected to the main controller 20. The display 50 is used to display the operating state of the conveying body 12, such as the power level, operating speed, mode, abnormal warnings, and so on.

After the above described preparatory steps are completed, the user may control the operation of the conveying body 12, such as operating the driving module 121 by controlling, for example, the speed controller 30, to insert the urinary catheter 11 into the genitalia of the user (e.g., for daily urination). When the user finishes the catheterization procedure and wishes to remove the urinary catheter, the same principles may apply. For example, the speed controller 30 may be used to control the operation of the driving module 121 to move the urinary catheter 11 away from the genitalia of the user and out of the conveying body 12. Due to the usage of the conveying body 12 and the clamping module 13, residual urine remaining inside the urinary catheter 11 is likely to flow out and cause a spillage within the clamping module 13. Therefore, the user may remove the clamping module 13 directly from the module accommodating groove 123, making the clamping module 13 work as a separate component. After removal, subsequent cleaning procedures may be performed. The components inside the clamping module 13 may be made of waterproof and rust-resistant materials, and the components may be designed to be permeable to water, allowing the user to directly soak the individual clamping module 13 in disinfectant solution or use other cleaning methods for overall disinfection. This maintains the cleanliness of the detachable urinary catheterization device 10, preventing bacterial infections. Additionally, the clamping module 13 may serve as a disposable/consumable device, saving time on cleaning and disinfection. This may also help saving costs associated with replacing the conveying body 12.

In summary, the urinary catheter, catheter sheath, and clamping channel of the present disclosure may be adjusted and replaced, according to the size of the user's genitalia. The clamping module may be an independent component, allowing users to quickly replace and clean the clamping module in the most convenient way. This not only addresses the problem of bacterial growth due to ineffective cleaning but also provides a detachable clamping module for easy usage by the users (or their family members) at home or in other medical facilities, thereby enhancing the convenience and flexibility in usage of the device.

The embodiments shown and described above are only examples. Many details are often found in the art. Therefore, many such details are neither shown nor described. Even though numerous characteristics and advantages of the present disclosure have been set forth in the foregoing description, together with details of the structure and function of the present disclosure, the present disclosure is illustrative only, and changes may be made in the details. It will therefore be appreciated that the embodiment described above may be modified within the scope of the claims.

What is claimed is:

1. A detachable urethral catheterization device for guiding a movement of a urinary catheter, comprising:
   a conveying body comprising a driving module, a conveying channel, and a module accommodating groove in communication with the conveying channel, the module accommodating groove including a first coupling component; and
   a clamping module coupled to the driving module, the clamping module having a second coupling component, wherein:
      the second coupling component is detachably coupled to the first coupling component in the module accommodating groove, and
      the driving module is configured to control the clamping module to clamp the urinary catheter and move the urinary catheter in the conveying channel and the module accommodating groove.

2. The detachable urethral catheterization device according to claim 1, wherein the first coupling component and the second coupling component are matching magnetic components, and the clamping module is defined as detachable via a magnetic attraction between the first coupling component and the second coupling component.

3. The detachable urethral catheterization device according to claim 1, wherein the clamping module comprises:
   a clamping body positioned within the module accommodating groove, the clamping body having a clamping channel that is correspondingly positioned within the conveying channel, and that is configured to accommodate the urinary catheter;
   a main driving component configured to couple to the driving module; and
   an auxiliary driving component, wherein:
      the main driving component and the auxiliary driving component are respectively located at two sides of the clamping channel,
      the main driving component and the auxiliary driving component contact an outer side of the urinary catheter,
      the driving module is configured to control the main driving component to move the urinary catheter, and
      the auxiliary driving component synchronously provides a moving assistance force based on a movement state of the urinary catheter.

4. The detachable urethral catheterization device according to claim 3, wherein the clamping channel is equipped with a limiting portion, and the limiting portion is configured to limit a moving direction and a deviation of the urinary catheter.

5. The detachable urethral catheterization device according to claim 3, wherein:
   the main driving component comprises a first coupling portion,
   the driving module comprises a second coupling portion,
   the first coupling portion and the second coupling portion include matching coupling structures, and
   when the first coupling portion is correspondingly coupled to the second coupling portion, the main driving component is coupled and fixed to the driving module.

6. The detachable urethral catheterization device according to claim 5, wherein the first coupling portion has a guiding inclined surface, and the guiding inclined surface is configured to guide the second coupling portion to be coupled and fixed to a coupling position of the first coupling portion.

7. The detachable urethral catheterization device according to claim 1, wherein:
   the clamping module is positioned within the module accommodating groove,
   a gap is between two outer sides of the clamping module and an inner wall of the module accommodating groove, and
   the gap is configured to ensure a central axis of the conveying channel and a central axis of the urinary catheter are coaxial.

8. The detachable urethral catheterization device according to claim 1, wherein:
   the conveying channel comprises a urinary catheter guiding portion and a urinary sheath accommodating portion,
   the module accommodating groove is located between the urinary catheter guiding portion and the urinary sheath accommodating portion,
   the urinary catheter guiding portion is configured to guide a movement path of the urinary catheter, the urinary sheath accommodating portion is configured to accommodate a urinary sheath, and a central axis of a through-hole of the urinary sheath is coaxial with a central axis of the urinary catheter.

9. The detachable urethral catheterization device according to claim 1, wherein:

the clamping module comprises a manual adjustment component, the manual adjustment component is configured to manually adjust a clamping force between the clamping module and the urinary catheter, and a movement range of the urinary catheter between the conveying channel and the module accommodating groove.

10. The detachable urethral catheterization device according to claim 1, wherein the conveying body further comprises:

a main controller electrically connected to the driving module, the main controller configured to control an operation of the driving module;

a speed controller electrically connected to the main controller, the main controller controlling a driving operation of the driving module according to an operating speed and mode of the speed controller;

a power controller configured to provide a power for an operation of components of the conveying body; and a display electrically connected to the main controller, the display configured to display an operational state of the conveying body.

* * * * *